United States Patent
Pilpel et al.

(10) Patent No.: US 11,246,579 B2
(45) Date of Patent: Feb. 15, 2022

(54) SYRINGE ASSEMBLY FOR STORING AND MIXING TWO COMPONENTS

(71) Applicants: Omrix Biopharmaceuticals Ltd., Rehovot (IL); Ethicon, Inc., Somerville, NJ (US)

(72) Inventors: Yair Pilpel, Rehovot (IL); Sivan Doron, Moshav Arugot (IL); Yuri Zherdev, Rehovot (IL); Lior Erez, Shoham (IL); Ashley DeAnglis, Skillman, NJ (US)

(73) Assignees: Omrix Biopharmaceuticals Ltd., Rehovot (IL); Ethicon, Inc., Somerville, NJ (US)

( * ) Notice: Subject to any disclaimer, the term of this patent is extended or adjusted under 35 U.S.C. 154(b) by 45 days.

(21) Appl. No.: 16/910,698

(22) Filed: Jun. 24, 2020

(65) Prior Publication Data

US 2020/0315601 A1    Oct. 8, 2020

Related U.S. Application Data (62) Division of application No. 15/366,230, filed on Dec. 1, 2016, now Pat. No. 10,716,548.

(60) Provisional application No. 62/262,537, filed on Dec. 3, 2015.

(30) Foreign Application Priority Data

Dec. 3, 2015 (IL) .................................... IL242924

(51) Int. Cl.
| | | |
|---|---|---|
| *A61B 17/00* | (2006.01) | |
| *A61M 5/19* | (2006.01) | |
| *A61M 5/32* | (2006.01) | |
| *A61M 5/315* | (2006.01) | |
| *A61B 17/88* | (2006.01) | |
| *A61K 38/00* | (2006.01) | |

(52) U.S. Cl.
CPC .... *A61B 17/00491* (2013.01); *A61B 17/8825* (2013.01); *A61M 5/19* (2013.01); *A61M 5/3294* (2013.01); *A61B 2017/00495* (2013.01); *A61B 2017/8838* (2013.01); *A61K 38/00* (2013.01); *A61M 5/31596* (2013.01)

(58) Field of Classification Search
CPC ........... A61B 17/8825; A61B 17/8838; A61M 5/3294

See application file for complete search history.

(56) References Cited

U.S. PATENT DOCUMENTS

| | | |
|---|---|---|
| 3,477,432 A | 11/1969 | Shaw |
| 3,741,383 A | 6/1973 | Wittwer |
| 3,785,379 A | 1/1974 | Cohen |
| 4,116,240 A | 9/1978 | Guiney |
| 4,676,775 A | 6/1987 | Zolnierczyk |

(Continued)

FOREIGN PATENT DOCUMENTS

| | | |
|---|---|---|
| WO | 98/033533 | 8/1998 |
| WO | WO02/095019 | 11/2002 |

(Continued)

OTHER PUBLICATIONS

International Search Report dated Mar. 17, 2017 for International Application No. PCT/IL2016/000023.

*Primary Examiner* — Anthony D Stashick
*Assistant Examiner* — Raven Collins
(74) *Attorney, Agent, or Firm* — David R. Crichton (57) ABSTRACT

The invention relates to syringes for storing and mixing components.

2 Claims, 6 Drawing Sheets

(56) References Cited

U.S. PATENT DOCUMENTS

| | | |
|---|---|---|
| 5,360,410 A | 11/1994 | Wacks |
| 6,121,232 A | 9/2000 | Nur et al. |
| 7,125,569 B2 | 10/2006 | Nur |
| 9,775,690 B2 | 10/2017 | Cheetham |
| 2010/0046315 A1 | 2/2010 | Merkhan |
| 2014/0058319 A1 | 2/2014 | Bartlett |
| 2014/0124534 A1 | 5/2014 | Gold |
| 2014/0378937 A1 | 12/2014 | Anderson |
| 2015/0343153 A1 | 12/2015 | Granelli |

FOREIGN PATENT DOCUMENTS

| | | |
|---|---|---|
| WO | 2011/089480 A1 | 7/2011 |
| WO | 2011/100852 A1 | 8/2011 |
| WO | 2017/093838 A1 | 6/2017 |
| WO | WO2017093838 A1 | 6/2017 |

SYRINGE ASSEMBLY FOR STORING AND MIXING TWO COMPONENTS

CROSS REFERENCE TO RELATED APPLICATION

This application is a divisional of co-pending U.S. application Ser. No. 15/366,230 filed Dec. 1, 2016, which is a Non-Provisional that claims the benefit of U.S. Provisional Application Ser. No. 62/262,537, filed Dec. 3, 2015 and claims benefit of Israeli Patent Application Number IL 242924, filed Dec. 3, 2015, the complete disclosure of which is hereby incorporated herein by reference for all purposes.

TECHNOLOGICAL FIELD

The presently disclosed subject matter relates to syringes for storing components and mixing them prior to their withdrawal from the syringe, e.g. for the administration of the mixture.

BACKGROUND

More particularly, the presently disclosed subject matter relates to syringes, in which two components are stored separately within a syringe container until they are mixed together therein to form a mixture ready for use. Often these components are in the form of an activator solution and an activatable solution, i.e. a solution that is capable of being activated by the activator.

U.S. Pat. No. 5,360,410 discloses a safety syringe for mixing a liquid solute and a drug substance stored in corresponding two compartments of the syringe separated by a stopper, which when dislodged from its place, allows the liquid solute from one compartment to inundate the drug substance in the other compartment.

US 2014/0058319A1 discloses a syringe for mixing substances stored in corresponding two compartments separated by a tearable membrane, which is torn when pulled by a lead wire or line that is attached to a removable outer sleeve or cap.

U.S. Pat. No. 3,785,379 also discloses the use of a membrane and piercing element disposed within a syringe for administration of mixed liquid and dry substance, wherein the dry substance and liquid are separably maintained in sealed relation one from the other until the membrane is pierced by the piercing element allowing the substances to be mixed.

US 2014/0124534 discloses a multi-compartment syringe apparatus for in-situ mixing of a plurality of products before use, wherein the compartments are of approximately the same volume and are separated by a one-way filter allowing passage of content only from the first compartment to the second compartment.

U.S. Pat. No. 4,116,240 discloses a mixing syringe comprising a container having a first compartment, a piston, a piston head having a second compartment, and a wall therebetween, and a plunger, wherein one material such as a liquid is stored in the compartment of the syringe container and another material such as a powder is stored in the compartment of the piston head. The wall is configured to be displaced by differential pressure during movement of the piston or by movement of the plunger.

U.S. Pat. No. 3,477,432 discloses a mixing syringe with an outer liquid retaining compartment, an inner liquid retaining compartment and a breakable seal therebetween, wherein breaking of the seal allows the contents of the compartments to be mixed.

U.S. Pat. No. 3,741,383 discloses a container comprising a first compartment for storing a liquid material; and a second compartment for storing a non-liquid material. One of the compartments is surrounded by the other compartment and is separated therefrom by a wall formed of a two-layer laminate. One layer of the laminate which is in contact with the liquid material is impervious to the liquid but penetrable. The inner layer of that laminate is rigid but soluble in the liquid, such that when the insoluble layer is pierced, the soluble layer comes into contact with the liquid and can thereupon be mixed with the liquid.

U.S. Pat. No. 4,676,775 discloses a fluid administration apparatus comprising a receptacle for storing fluid and a fluid administration conduit assembly having a hollow fluid administration tube, a handle and a hollow spike unit extending axially outwardly from the handle. The receptacle comprises two fluid chambers separated by a pierceable membrane. Piercing the membrane by the spike facilitates the mixing of the fluids from the two chambers.

GENERAL DESCRIPTION

According to one aspect of the presently disclosed subject matter, there is provided a syringe assembly for mixing a first and a second components, comprising prior to its use:
  a syringe container having a proximal end, a distal end, a cavity extending therebetween along a longitudinal axis, and an outlet at the distal end in fluid communication with the cavity;
  a receptacle disposed within the cavity at a location spaced from the distal end of the container, the receptacle containing the first component;
  a ruptureable membrane constituting at least a part of the receptacle and sealingly separating the receptacle from an operative portion of the cavity, the operative portion is disposed between the membrane and the distal end of the container, the operative portion containing the second component;
  a punching and mixing device disposed inside the operative portion of the cavity and comprising:
    a punching tip facing the membrane for piercing it when the punching tip is moved into its punching position in the direction away from the distal end of the container, thereby rupturing the membrane to release the first component into the operative portion of the cavity, the released first component and the second component constituting a content of the operative portion of the cavity;
    a mixing stirrer disposed between the punching tip and the distal end of the container and capable of stirring the content of the operative portion of the cavity, when being moved along the longitudinal axis at least in one direction, to facilitate the mixing of the first and second components; and
  a manipulation arrangement for manipulating the punching and mixing device to move the punching tip into its punching position and to move the mixing stirrer at least along the longitudinal axis at least in one direction, the manipulation arrangement being configured for being disassembled from the syringe container from the syringe.

The above structure of the syringe assembly and, particularly, the fact that it includes the mixing stirrer movable along the longitudinal axis, allows homogeneous mixing of the first and second components with a reduced risk of generating a foam during the mixing, which can be particularly advantageous when the components have a relatively high viscosity.

In addition, the above described mutual disposition of the mixing stirrer and the punching tip relative to the ruptureable membrane of the receptacle and the operative portion of the cavity, allows the component disposed within the receptacle, when released therefrom, to move into the operative portion of the cavity towards the mixing stirrer, thereby further facilitating the mixing.

The stirrer can be movable in two directions along the axis and/or be rotatable about the longitudinal axis, to facilitate the stirring.

The manipulation arrangement can comprise a shaft, the shaft extending along the axis and via said outlet between a shaft distal end disposed outside the syringe container and configured for applying thereto a manipulating movement, and a shaft proximal end on which the punching and mixing device is fixed inside the operative cavity. This arrangement allows simultaneous movement of the punching tip and the mixing stirrer, reducing the time needed for the beginning of the mixing.

The shaft can be movable by the manipulation arrangement between an outermost position of the shaft, in which the shaft projects outwardly from the outlet of the container to a first extent, and an innermost position of the shaft, in which the shaft projects outwardly from the outlet of the container to a second extent smaller than the first extent. For this purpose, the manipulation arrangement can comprise an actuator connected to the distal portion of the shaft for applying an axial pressing force thereto, it moves the shaft into its innermost position and releasing the force to allow the shaft to return into its initial outermost position.

The manipulation arrangement can be configured for being separated from the syringe container, thereby allowing the withdrawal of the mixture from the outlet of the container. This can be achieved, for example, by forming the distal end of the container with a distal end surface, and allowing the punching and mixing device to be detachable from at least the proximal end of the shaft when the shaft is moved outwardly from the container through the outlet with the mixing stirrer abutting the distal end surface. In this case, fluid communication should be maintained between the cavity and the outlet of the container, which can be provided by means of a channel formed in the mixing stirrer. This arrangement allows withdrawing the mixture from the syringe container outlet without the necessity of removing the punching and mixing device therefrom.

The punching and mixing device can have a sleeve extending distally from the mixing stirrer and configured to receive therein a portion of the shaft associated with its proximal end. The sleeve can be in fluid communication with the operative cavity, via a corresponding channel in the mixing stirrer. The sleeve can have an outer diameter smaller than that of the outlet. This arrangement allows using the sleeve for withdrawing the mixture of the two components from the syringe container, when the manipulation arrangement has been dissembled therefrom.

The manipulation arrangement can comprise an actuator connected to the distal portion of the shaft for applying an axial pressing force thereto to move the shaft towards and into its innermost position and releasing the force to allow the shaft to return towards and into its initial outermost position. The actuator can be provided with a removable actuator safety catch, to prevent the actuator from applying the axial pressing force to the distal portion of the shaft until the catch is removed.

When the syringe container is to be used for administration the mixture of the two components, after the manipulation device has been dissembled therefrom, the container can have an opening at its proximal end, and the assembly can comprise a plunger passing through the opening so as to be movable along the longitudinal axis, the plunger having a plunger distal end sealingly received within the container, and a plunger proximal end disposed outside the cavity so as to allow applying to the proximal end a plunger moving axial force.

The plunger can be provided with a removable safety stopper disposed between the plunger proximal end and the opening to prevent the plunger from its movement inwardly with respect to the container until the stopper is removed.

The receptacle can constitute, or be attached to, or be disposed within, the distal end of the plunger.

In accordance with another aspect of the presently disclosed subject matter, a kit for use with a receptacle containing a first component and comprising a ruptureable membrane constituting at least a part of the receptacle, for assembling a syringe for mixing the first component with a second component, the kit comprising:
  a syringe container having a proximal end and a distal end and a cavity extending therebetween along a longitudinal axis, the cavity being configured for:
    receiving therein the receptacle within the cavity closer to the proximal end of the container than to its distal end, so that the membrane sealingly separates the receptacle from the operative portion of the cavity disposed between the receptacle and the distal end of the container; and
    receiving in the operative portion of the cavity the second component;
  a punching and mixing device configured for being mounted inside the operative portion of the cavity and comprising:
    a punching tip configured for piercing the membrane when the punching tip is facing it and moved into its punching position in the direction away from the distal end of the container, thereby rupturing the membrane to release the first component into the operative portion of the cavity, the released first component and the second component constituting a content of the operative portion of the cavity;
    a mixing stirrer disposed between the punching tip and the distal end of the container and capable of stirring the content of the operative portion of the cavity, when being moved along the longitudinal axis at least in one direction, to facilitate the mixing of the first and second components; and
  a manipulation arrangement for manipulating the punching and mixing device to move the punching tip into its punching position and to move the mixing stirrer at least along the longitudinal axis at least in one direction.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

FIGS. 1 to 3C illustrate a syringe assembly generally designated as 1, for mixing two components to produce a homogeneous mixture. The components can be of the kind, which once mixed, produce a curable substance, in which case a first component can be capable of being activated by the second component. Once the desired mixture or substance is produced, the syringe assembly is to be used for its administration as required. Thus, the syringe assembly 1 has an initial state (prior to mixing the two components), a mixing state (in which mixing the two components is performed), and an administration state (in which the syringe assembly is ready for the administration of the substance produced by the mixture of the two components).

Figure 1:
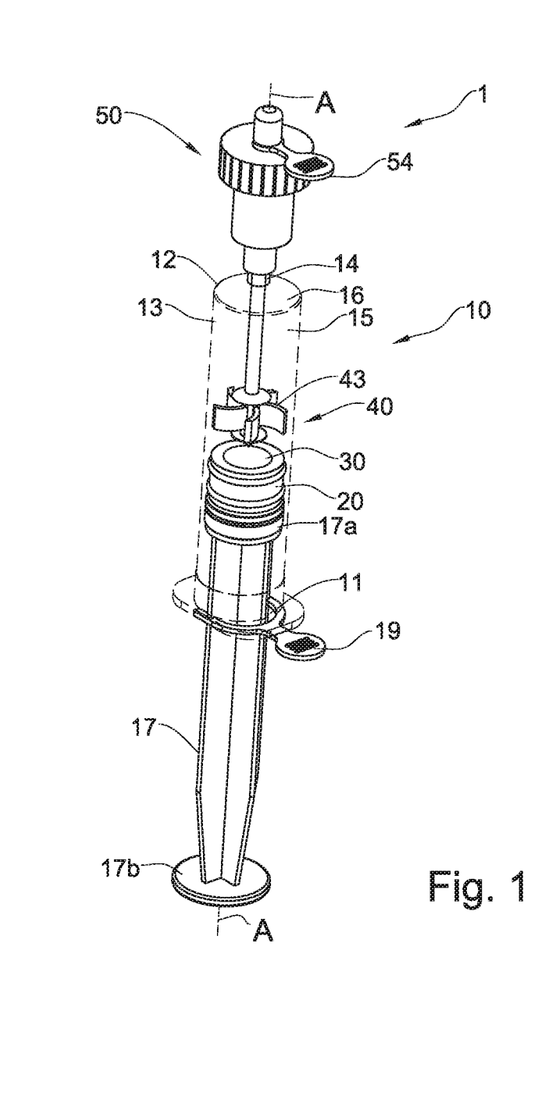
FIG. 1 is a perspective view of a syringe assembly according to one embodiment of the presently disclosed subject matter.
Figure 2:
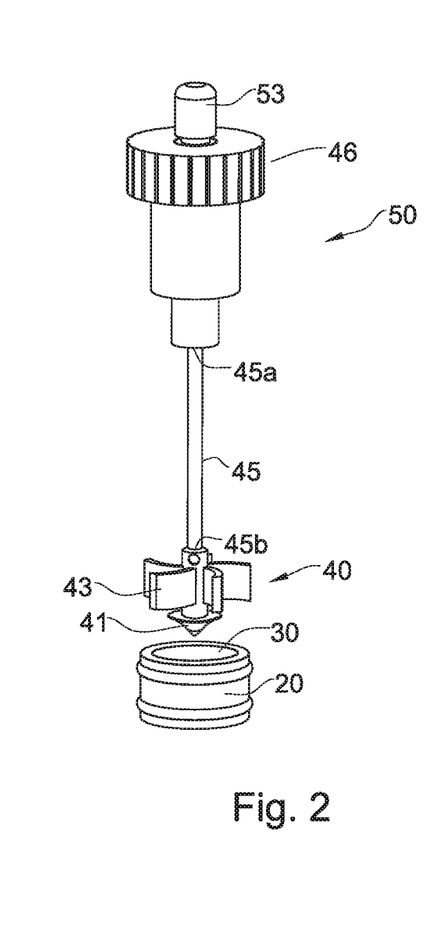
FIG. 2 is a perspective view of a punching and mixing unit of the syringe assembly shown in FIG. 1, including a punching and mixing device, a manipulation arrangement and a receptacle.

With reference to FIGS. 1 to 3A, the syringe assembly 1 in its initial state comprises:

- a syringe container 10 having an open proximal end 11, a distal end 12 with an outlet 14 surrounded by a distal end surface 16, and a syringe cavity 15 extending between the two ends along a longitudinal axis A;
- a plunger 17 partially received within the syringe cavity 15 via the open end 11 and having a plunger distal end 17a disposed within the cavity 15 and a plunger proximal end 17b disposed outside the cavity, the plunger being movable from an initial position at the initial state of the assembly, in which the plunger distal end 17a is disposed adjacent the proximal end 11 of the container 10, and a final position, in which the plunger distal end 17a is spaced from the proximal end 11 of the container 10 to a maximal extent at the administration state of the assembly;
- a receptacle 20 having a receptacle cavity 21 (FIG. 3A) accommodating the first component, and disposed within the syringe cavity 15 adjacent and/or in the plunger distal end 17a so that a cavity operative portion 13 is created in the syringe cavity 15 between an area 30 of the receptacle 20 facing towards the distal end 12, and the outlet 14 of the syringe container, where the second component is accommodated;
- a movable punching and mixing device 40 (FIG. 2) disposed inside the operative portion of the cavity and comprising a punching tip 41 facing the receptacle 20 for piercing it to release the first component into the operative portion of the cavity, and a mixing stirrer 43 disposed between the punching tip and the distal end 12 of the container 10 for stirring the content of the operative portion of the cavity; and
- a manipulation arrangement 50 detachably attached to the punching and mixing device 40, constituting therewith a punching and mixing unit shown separately in FIG. 2, for manipulating the punching and mixing device 40 in the mixing state of the assembly, and for being dissembled from the punching and mixing device 40 and from the syringe container 10, to bring it into the administration state.

The entire receptacle 20 or its area 30 or only a portion of this area is made of a ruptureable material capable of being plastically deformed at least at that area, e.g. being broken, torn, disrupted or penetrated so as to provide access therethrough to the interior of the receptacle. The area 30 thus constitutes a membrane, which can be ruptured from the direction of the operative portion 13 of the syringe cavity and thereby create a fluid communication between the receptacle cavity 21 and the operative portion 13. The membrane 30 can be a pre-tensioned membrane. Typically, once ruptured the tensioned membrane will retract towards its circumference, thereby widening the ruptured area. The receptacle 20 can be configured to maintain its integrity at areas other than the ruptured area of the membrane 30. Alternatively, the receptacle 20 can be configured to collapse when ruptured, as long as this does not interfere with the release of the first component into the operative portion of the cavity.

Figure 3A:
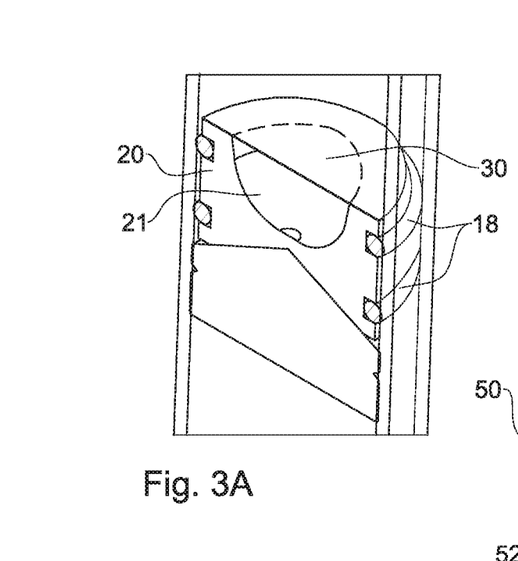
FIG. 3A is an enlarged cross-sectional view of a receptacle of the syringe assembly shown in FIG. 1.
Figure 3B:
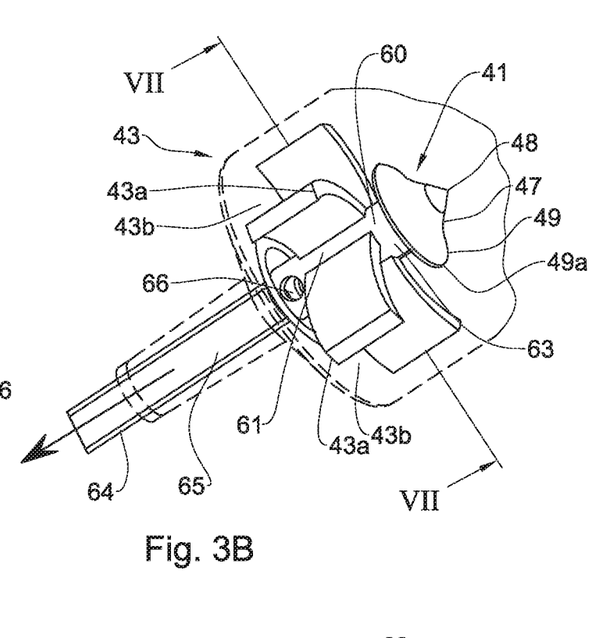
FIG. 3B is an enlarged perspective view of the punching and mixing device shown in FIG. 2.

The receptacle cavity 21 can have a shape facilitating the release of the first component therefrom once the membrane 30 is ruptured. For example, this can be a semispherical shape as shown in FIG. 3A.

The receptacle can be configured to be sealingly received within the syringe cavity for preventing fluid communication between the cavity operative portion 13 and the open proximal end 11 of the container. Such sealing can be provided by any suitable known means such as e.g. one or more O-rings 18 (FIG. 3A) mounted on the circumference of the receptacle 20 and holding it firmly in place within the syringe cavity 15. Alternatively, or in addition, a sealing can be provided at the plunger distal end 17a received within the syringe cavity 15. The receptacle 20 can be attached to or mounted in the plunger distal end 17a.

The plunger 17 can further be provided with a removable safety stopper 19 disposed between the plunger proximal end 17b and the syringe proximal end 11 to prevent the plunger from its occasional movement inwardly into the syringe cavity 15 until the stopper is removed.

The punching tip 41 and the mixing stirrer 43 of the punching and mixing device are held at fixed distance from each other by a common rod 60.

This distance can be in the range of 0.25 to 0.75 of the length of the syringe cavity 15. As best seen FIG. 3B, in the described example, the punching tip 41, the mixing stirrer 43 and the rod 60 are all produced as a unitary body as shown in FIG. 2, made of a rigid material such as plastic. Alternatively, these elements can be produced separately and assembled to form the punching and mixing device 40. In addition or alternatively, the elements can be made of different materials corresponding to their functions. For example, the mixing stirrer 43 can be made of a semi-rigid material in order to reduce foaming during mixing the punching tip 41 can at least partially be made of a rigid material.

The punching tip 41 (FIG. 3B) has a proximal sharp apex 48 configured for punching the membrane 30, a distal wide skirt 49, and a tip body 47 extending therebetween. The tip body 47 can have a shape complementary to that of the receptacle cavity 21 (not shown), so as to facilitate the release of the contents of the receptacle towards the operative portion 13 of the cavity. The skirt 49 can have a flexible edge 49a, e.g. due to the skirt's circumference being thinner than its central area, allowing thereby the skirt's edge to change its orientation when contacting the membrane 30, to further facilitate the release of the content of the receptacle into the operative portion 13 of the cavity during the mixing operation. The sharp apex 48 and, optionally, the tip body 47 of the punching tip 48 can be made of a rigid material, whilst the distal wide skirt 49 can be made of a flexible material.

The mixing stirrer 43 has such a form as to allow fluid such as the first and second components or their mixture, to pass through and/or around the stirrer, when it is moved axially and, optionally, when it is rotated. In a described example, the stirrer is in the form of a rotor and a plurality of curved angled blades 43a spaced from each other by passages 43b. Alternatively, the blades can be straight and have planar surfaces and/or they may not be angled. In another example, the mixing stirrer can be in the form of a disc with a pattern of holes or slots.

The rod 60 (FIG. 3B) has a hub section 61 surrounded by the mixing stirrer 43, a rod proximal section 63 extending between the punching tip 41 and the mixing stirrer 43, and a rod distal section 64 (FIG. 3C) projecting distally from the mixing stirrer 43. The rod distal section 64 has the form of a hollow sleeve terminating at a sleeve outlet 62 (FIG. 3D), which is in fluid communication with the operative portion 13 of the syringe cavity. One possible manner, in which such fluid communication can be provided is a channel 65 (FIG. 3B) in the hub section 61 connecting an opening 66 made in the hub, with the hollow interior of the sleeve 64.

Figure 3C:
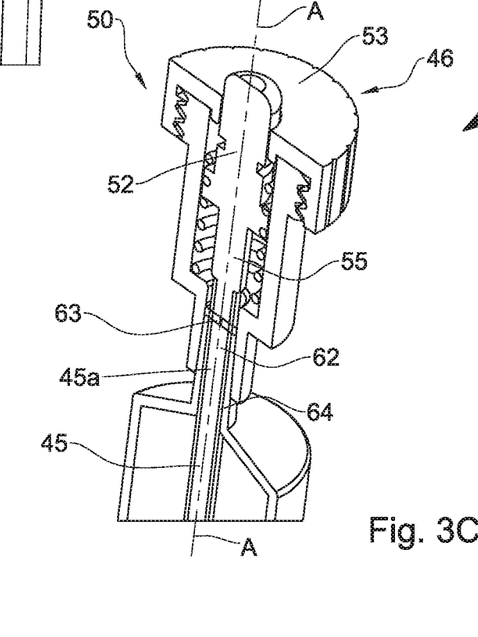
FIG. 3C is an enlarged cross-sectional view of a manipulation head of the manipulation arrangement shown in FIG. 2, including a rod whose distal end is in the form of a sleeve.

With reference to FIGS. 1, 2 and 3C, the manipulation arrangement 50 comprises a manipulation head 46 and a shaft 45 having a shaft distal end 45a received within the manipulation head 46 and a shaft proximal end 45b tightly received within the rod distal section 64. The manipulation head 46 is configured for moving the shaft 45 and, consequently, the punching and mixing device 40, along the longitudinal axis A and, optionally, rotating it about the longitudinal axis A.

The manipulation head 46 comprises an actuator 52 for applying to the shaft an axial pressing force, to move the shaft 45 with the rod distal section 64 into their innermost position with respect to the cavity operative portion 13 of the syringe cavity 15, in which the punching tip 41 is pressed into the area 30 of the receptacle 20, and for releasing the force to allow the shaft to return, into its initial position. The actuator 52 can allow moving the shaft with the rod distal section into any intermediate position between their innermost and initial positions, by applying a reduced pressing force or limiting the releasing force, respectively. In the described example, the actuator 52 is in the form of a springed button 53 having a stem 55 received within the manipulation head 46 and connected to or integrally formed with the shaft distal end 45a.

The manipulation arrangement 50 can further comprise a removable actuator safety catch 54 (FIG. 4A), to prevent the actuator 52 from applying the axial pressing force to the shaft 45 until the stopper is removed.

The manipulation head 46 with the shaft 45 can be rotated manually or automatically (not shown).

The above described elements of the syringe assembly 1 have the following dimensions:

Dc—diameter of the operative cavity 13;

Lc—axial length of the operative cavity in the initial state of the syringe assembly, which is defined by a distance between the membrane 30 and the distal end 12 of the syringe container;

Do—diameter of the outlet 14;

$D_{sh}$—diameter of the shaft 45;

$D_s$—outer diameter of the sleeve 64, which is either smaller than the diameter Do of the outlet 14 such as to allow the sleeve to pass freely through the outlet 14 (in case the sleeve has a length that does not exceed the distance between the hub 61 of the mixing stirrer 43 and the distal end surface 16 of the syringe container so that it is fully accommodated within the operative cavity 13 in the initial state of the syringe assembly), or which essentially equals the diameter Do of the outlet 14 so as to allow the sleeve 64 to be tightly received within the outlet 14 (in case the sleeve has a length that is greater than the distance between the hub 61 of the mixing stirrer 43 and the distal end surface 16 of the syringe container so that it protrudes distally from the outlet 14 in the initial state of the syringe assembly);

$d_s$—inner diameter of the sleeve 64, which essentially equals the diameter $D_{sh}$ of the shaft 45, so as to ensure that a portion of the shaft including its distal end 45a is tightly received within the sleeve 64;

$D_m$—maximal diameter of the mixing stirrer 43, which is in the range $0.25Dc \leq Dm < Dc$. For example, the range can be $0.5Dc \leq Dm \leq 0.95Dc$, and more particularly $0.7Dc \leq Dm \leq 0.9Dc$.#

In the above description, all the diameters are meant to be measured in a plane perpendicular to the axis A of the syringe assembly and, if in that plane the shape of an element to which the diameter refers, is not circular, the diameter should be considered as being that of a circle inscribed in such an element. For example, if the operative cavity 13 is not circular in its cross-sectional plane taken perpendicular to the axis A, its diameter Dc is that of a circle inscribed in the operative cavity in such a plane.

Figures 4A, 4B:
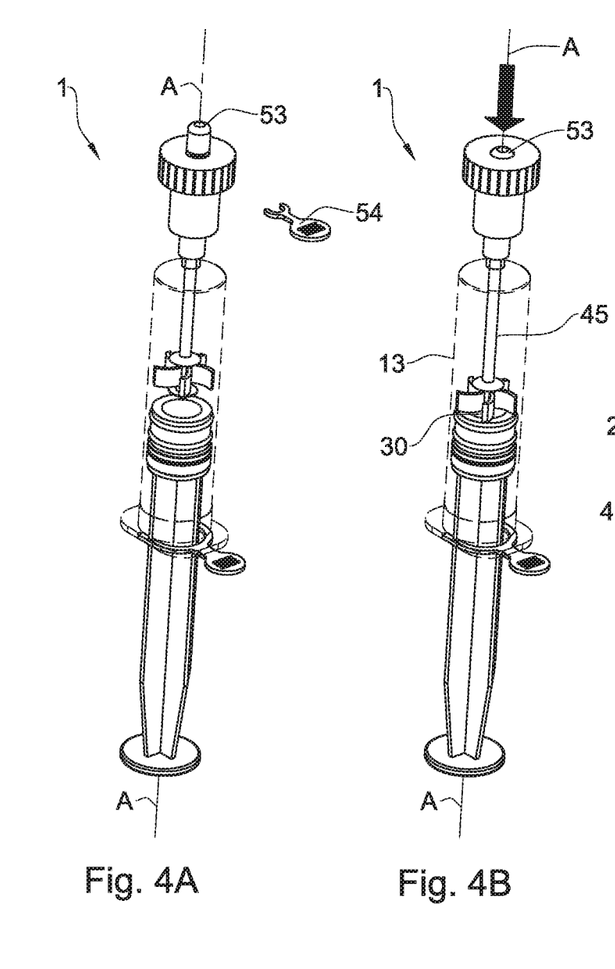
FIGS. 4A to 4D illustrate the manner, in which mixing is performed in the syringe assembly shown in FIG. 1.
Figure 4C:
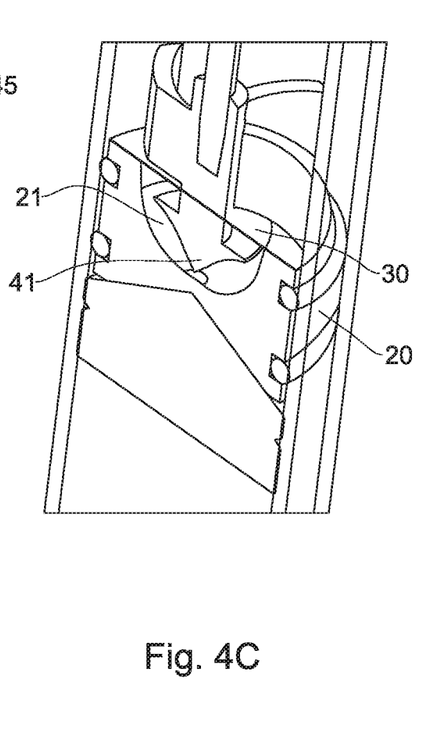

With reference to FIGS. 4A to 4D, in order to have the first and second components mixed in the syringe assembly as described above, the following steps are to be performed:

(a) the actuator safety catch 54 is removed to allow pressing the springed button 53 of the actuator 52 (FIG. 4A);

(b) the springed button 53 of the actuator 52 is pressed, thereby applying axial force to the shaft 45 and moving it together with the punching and mixing device 40, along the longitudinal axis A into their innermost position with respect to the operation portion 13 of the syringe cavity 15, in which the punching tip 41 is pressed into the membrane 30 of the receptacle 20 and the membrane 30 is ruptured; this results in the release of the first component disposed in the receptacle cavity 21 (FIGS. 4B and 4C).

Figure 4D:
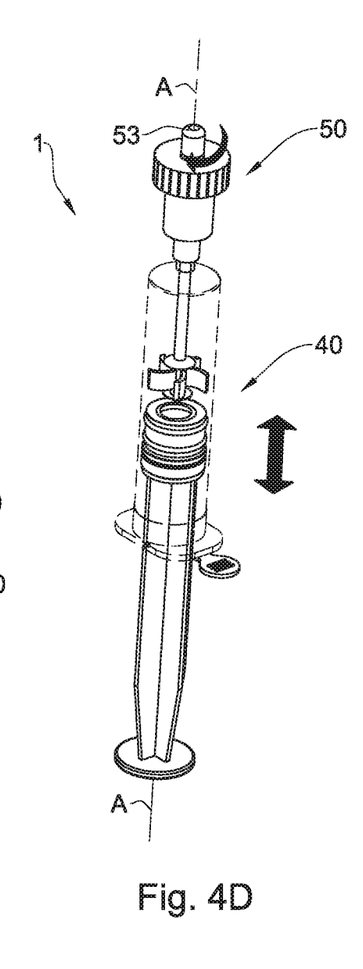

(c) releasing the button 53, thereby allowing the shaft 45 to return to its initial position;

(d) pressing and releasing the button 53 again as many times as needed to facilitate the mixing of the two components (FIG. 4D); and (e) optionally, rotating the manipulation head 46 about the longitudinal axis A, thereby rotating the punching and mixing device 40, to further facilitate the mixing (FIG. 4D).

Figure 5A:
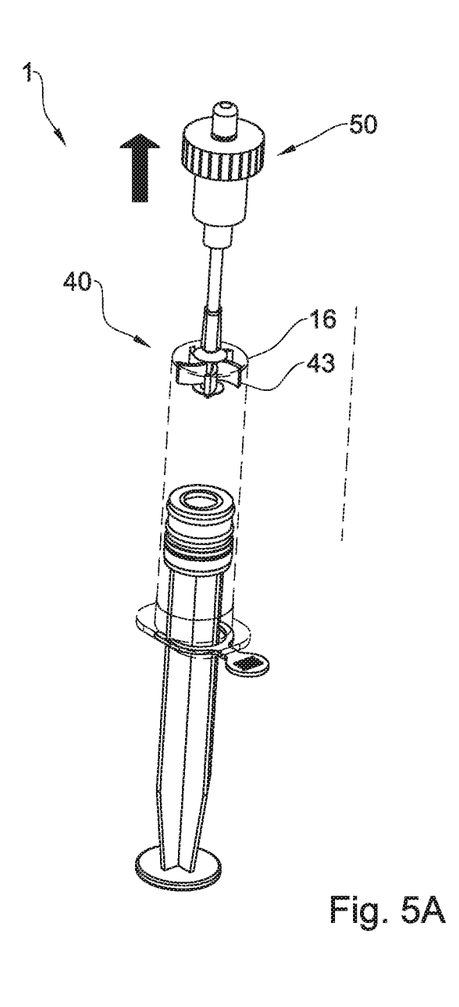
FIGS. 5A to 5C illustrate the manner, in which the syringe assembly shown in FIGS. 4A to 4D is brought into a state, in which its contents can be administered.
Figure 5B:
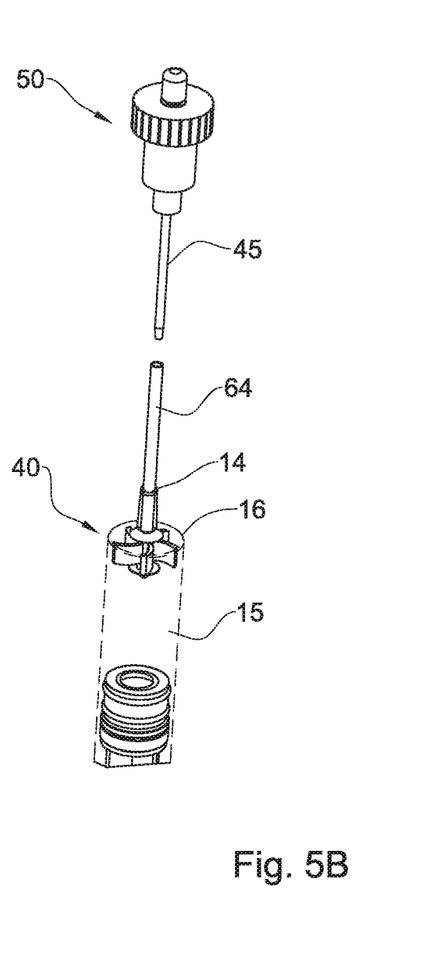
Figure 5C:
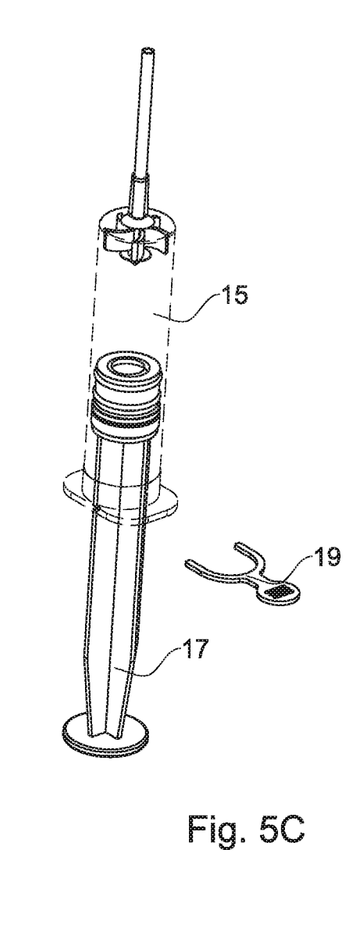

Once the two components have been mixed, the syringe assembly can be brought into its administration state by the following steps illustrated in FIGS. 5A to 5C:

(i) pulling the manipulation arrangement 50 with the punching and mixing device 40 in the distal direction until the mixing stirrer 43 abuts the distal end surface 16 of the syringe container (FIG. 5A); in this position the sleeve 64 projects to a maximal extent from the outlet 14 of the syringe container;

(ii) continuing pulling the manipulation arrangement 50 until the shaft 45 is removed out of the sleeve 64 (FIG. 5B); and (iii) removing the plunger safety stopper 19 to allow the plunger 17 to move inwardly into the syringe cavity 15.

Figures 6A, 6B:
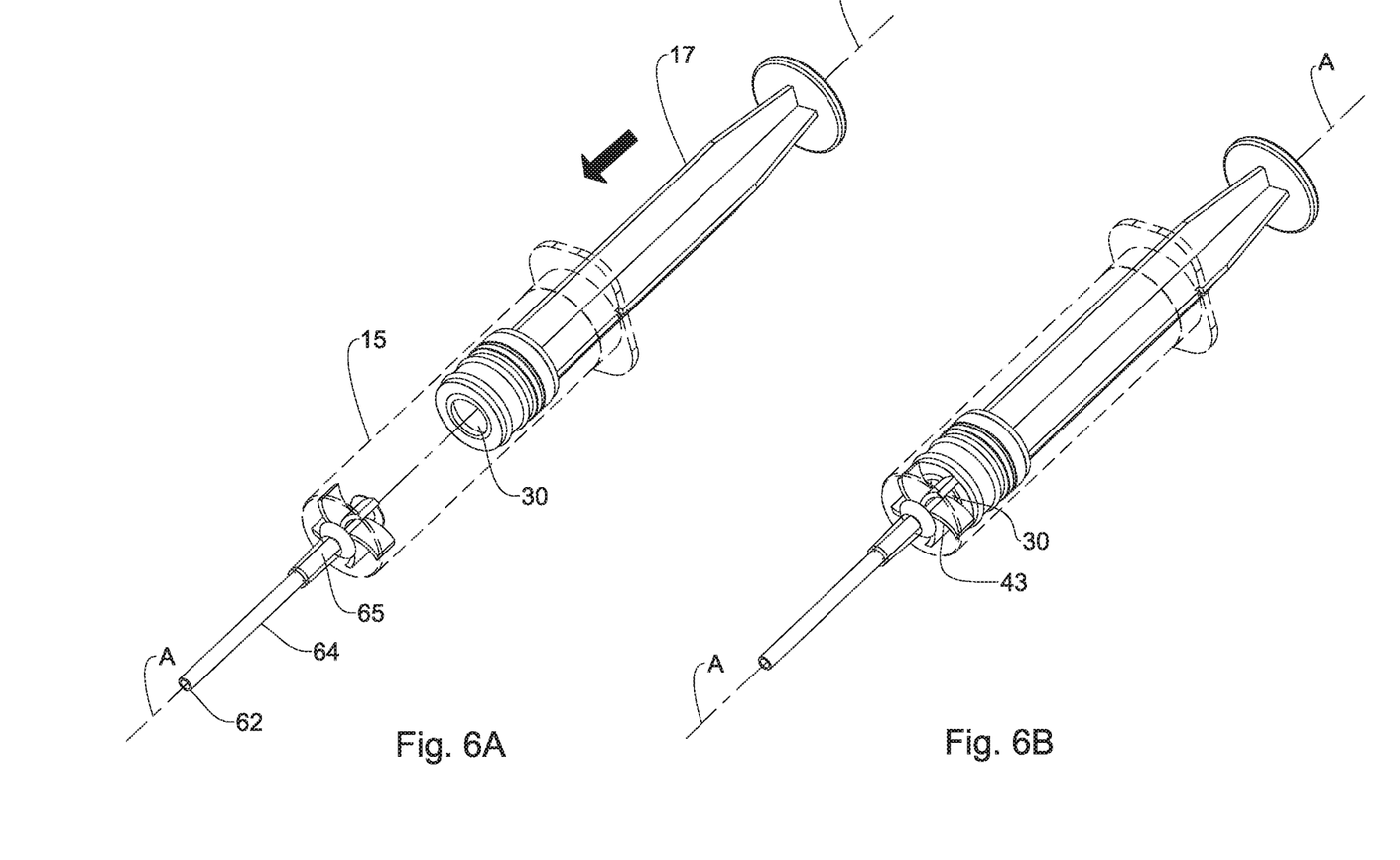
FIGS. 6A and 6B illustrate the manner in which administration can be performed using the syringe assembly shown in FIG. 5C.

In this position, the syringe assembly is in its administration state (FIG. 6A), and its content can be administered through the outlet 62 of the sleeve 64, which is in fluid communication with the syringe cavity 15 via the channel 65 in the hub of the mixing stirrer 43, by the axial movement of the plunger in the distal direction until the receptacle membrane 30 or its remainder abuts the punching and mixing device 40 (FIG. 6B).

Figure 3D:
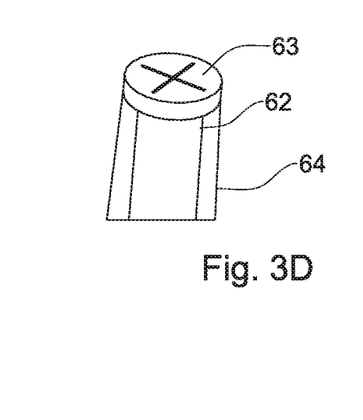
FIG. 3D is an enlarged perspective view of the sleeve shown in FIG. 3C.

In an alternative embodiment of the syringe assembly according to the presently disclosed subject matter, the punching and mixing device 40 can be formed without the sleeve 64 but rather it can be held directly by the shaft 45, whose proximal end 45b can be received within the hub 61 of the mixing stirrer 43, in which case the channel 65 will provide fluid communication between the syringe cavity 15 and the outlet 14 of the syringe container and its content will be administered therethrough. In such embodiment, the outlet 14 can extend distally from the distal end 12 of the syringe container to any desired extent. In addition, the outlet 14 of the syringe container 10 can be provided with a sealing pierced septum 63, as shown in FIG. 3D, to prevent occasional exposure of the contents of the syringe assembly to its exterior. The pierced septum 63 can be made of an elastic material such as, for example, silicone. An administration element can be mounted on the outlet 14.

It needs to be noted that in this embodiment it is important to ensure that the punching and mixing device 40 does not change its orientation inside the cavity 15 when it detaches from the shaft 45 to bring the syringe assembly into its administration state, because such change of orientation can prevent the plunger 17 from taking its desired distal position for administration of the content of the syringe assembly.

Figures 7, 8:
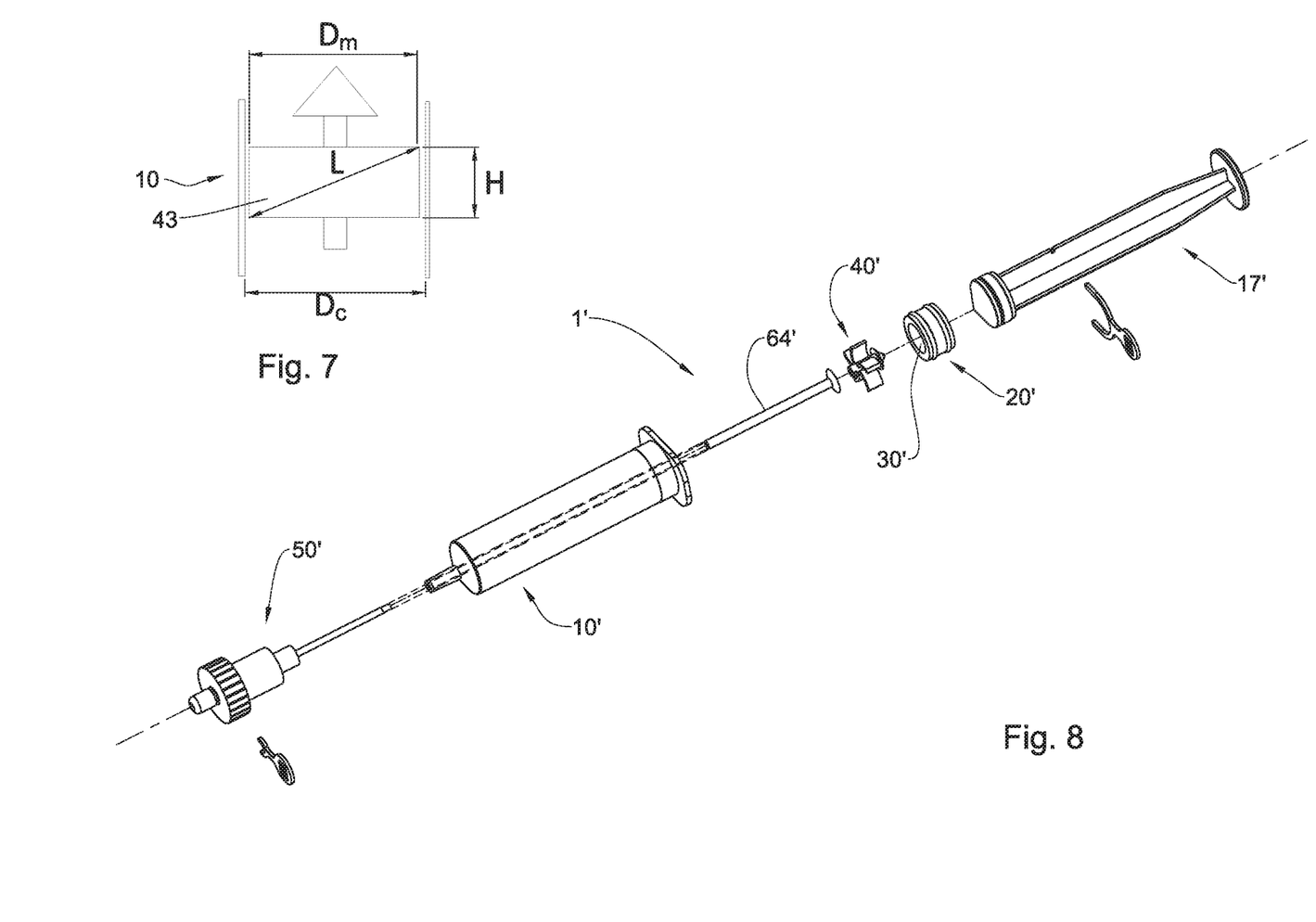
FIG. 7 is a schematic cross-sectional view of a portion of the syringe assembly shown in FIG. 3B, taken along a plane VII-VII.
FIG. 8 illustrates a kit comprising components, from which an assembly of the kind shown in FIG. 1, can be assembled.

With reference to FIG. 7, the above change of orientation can be prevented by designing the mixing stirrer so that its parameters meet the following three conditions:

$L > D_c;$ $D_m < D_c;$ #and $H \geq \sqrt{L^2 - D_m^2} = \sqrt{L^2 - D_c^2};$ where:

L is diagonal extension of the mixing stirrer 43 in its cross-section along a plane passing through its maximal diameter and including the axis A;

$D_c$ is diameter of the operative cavity 13;

$D_m$ is maximal diameter of the mixing stirrer 43; and

H is maximal extension of the mixing stirrer along the axis A.

For example, for a syringe assembly with $D_c$=15.8 mm and $D_m$ almost equal to $D_c$, L can be chosen to be L=16 mm and H can be not less than 2.5 mm. In case, $D_m$=15.4 mm, the extension H of the stirrer 43 is not less than 4.3 mm.

According to another aspect of the presently disclosed subject matter, there can be provided a kit for assembling a syringe for mixing the first component with the second component, which can comprise all or a part of the elements of the syringe assembly 1 described above. One example of such kit 1' is shown in FIG. 8, and it comprises a syringe container 10', a plunger 17', a receptacle 20' with a ruptureable membrane 30' separate from or as an integral unit with the plunger 17' containing the first component, a punching and mixing device 40' with or without a sleeve 64', a manipulation arrangement 50' and a package with the second component, all similar to the respective elements described above.

The above described syringe assemblies are designed so that a volume V of the operative portion 13 of the cavity is greater than a volume v within which the second component is disposed in the receptacle 20. In a particular design, their ratio V:v can be in the range of 10 to 200.

The above described syringe assemblies can particularly be used in applications where the second component is chemically inactive and the first component is an activator for the second component.

For example, the first component can be calcium chloride and the second component can be, for example, Prothrombin-Proconvertin-Stuart Factor-Antihemophilic Factor B (PPSB) and fibrinogen stabilized by sodium citrate, in which case, upon mixing the two components in the syringe assembly, the PPSB zymogens will become activated.

In a further example, the first component can be anti-sense DNA complementary to a thrombin binding aptamer, and the second component can be thrombin stabilized by a thrombin binding aptamer which prevents autocatalysis. Upon mixing the two components in the syringe assembly, the activity of the thrombin would be restored.

In a still further example, the first component can be an agent which activates fibrinogen, such as, for example, thrombin or a substance obtainable from snake venom at low activity/concentration and the second component can be fibrinogen/BAC2. Upon mixing the two components in the syringe assembly, the thrombin would enzymatically act on the fibrinogen to form fibrin. At lowest levels of thrombin, for example, 1 U, the fibrin polymerization time will be relatively slow, i.e., minutes, allowing the activated BAC2 to be delivered for hemostasis, sealing or tissue adhesion applications.

For embodiments wherein the first component comprises thrombin and the second component comprises fibrinogen, one or both of the components can optionally be prepared from an initial blood composition. The blood composition can be whole blood or blood fractions, i.e. a fraction of whole blood such as plasma. The origin of the fibrinogen and thrombin can be autologous whereby they would be manufactured from the patient's own blood or from pooled blood or blood fractions. It is also possible that the components are prepared by recombinant methods.

In one embodiment of the invention, the fibrinogen component comprises a biologically active component (BAC) which is a solution of proteins derived from blood plasma, optionally further comprising anti fibrinolytic agents such as tranexamic acid and/or stabilizers such as arginine, lysine, pharmaceutically acceptable salts thereof, or mixtures thereof. BAC is optionally derived from cryoprecipitate, in particular concentrated cryoprecipitate. The term "cryoprecipitate" refers to a blood component which is obtained from frozen plasma prepared from whole blood, recovered plasma or from source plasma which is collected by plasmapheresis. A cryoprecipitate is optionally obtained when frozen plasma is slowly thawed in the cold, typically at a temperature of 0-4° C., resulting in the formation of precipitate that contains fibrinogen and factor XIII. The precipitate can be collected, for example, by centrifugation and dissolved in a suitable buffer such as a buffer containing 120 mM sodium chloride, 10 mM trisodium citrate, 120 mM glycine, 95 mM arginine hydrochloride, 1 mM calcium chloride. The solution of BAC optionally comprises additional factors such as for example Factor VIII, Factor XIII, fibronectin, von Willebrand factor (vWF), vitronectin, etc. for example as described in U.S. Pat. No. 6,121,232 and WO9833533. The composition of BAC optionally comprises stabilizers such as tranexamic acid and arginine hydrochloride. The amount of tranexamic acid in the solution of BAC is optionally in the range of from about 80 to about 110 mg/ml. The amount of arginine hydrochloride is optionally in the range of from about 15 to about 25 mg/ml.

Optionally, the solution is buffered to a physiological compatible pH value. The buffer can comprise glycine, sodium citrate, sodium chloride, calcium chloride and water for injection as a vehicle. Glycine is optionally present in the composition at a concentration in the range of from about 6 to about 10 mg/ml; sodium citrate is optionally present at a concentration in the range of from about 1 to about 5 mg/ml; sodium chloride is optionally present at a concentration in the range of from about 5 to about 9 mg/ml; and calcium chloride is optionally present at a concentration in the range of from about 0.1 to about 0.2 mg/ml.

In one embodiment of the invention, the fibrinogen component is derived from blood. In some other embodiments, BAC is a biologically active component that does not contain tranexamic acid. This is considered a second generation BAC and is referred to in the art as BAC2. In another embodiment of the invention, the concentration of plasminogen and/or plasmin in the blood derived component comprising fibrinogen is lowered. The removal of plasmin and plasminogen from the blood derived component can be carried out as described in U.S. Pat. No. 7,125,569 and WO02095019.

The thrombin component optionally comprises calcium chloride, human albumin, mannitol, sodium acetate and water for injection.

We claim:

1. A syringe assembly for mixing a first and a second components, comprising prior to its use:

a syringe container having a proximal end, a distal end, a syringe cavity extending therebetween along a longitudinal axis (A), and an outlet at the distal end in fluid communication with the syringe cavity;

a receptacle disposed within the syringe cavity at a location spaced from the distal end of the container, the receptacle containing the first component;

a ruptureable membrane constituting at least a part of the receptacle and sealingly separating the receptacle from an operative portion of the syringe cavity, the operative portion is disposed between the membrane and the distal end of the syringe container, the operative portion containing the second component;

a punching and mixing device disposed inside the operative portion of the syringe cavity and comprising:

a punching tip facing the membrane for piercing it when the punching tip is moved into its punching position in the direction away from the distal end of the container, thereby allowing rupturing the membrane to release the first component into the operative portion of the syringe cavity, the released first component and the second component constituting of a mixture;

a mixing stirrer disposed between the punching tip and the distal end of the container and capable of stirring the content of the operative portion of the syringe cavity, when being moved along the longitudinal axis at least in one direction, to facilitate the mixing of the first and second components; and a manipulation arrangement for manipulating the punching and mixing device to move the punching tip into its punching position and to move the mixing stirrer at least along the longitudinal axis at least in one direction, wherein the container has an opening at its proximal end, and the assembly further comprises a plunger passing through the opening so as to be movable along the longitudinal axis, the plunger having a plunger distal end sealingly received within the container, and a plunger proximal end disposed outside the syringe cavity so as to allow applying to the proximal end a plunger moving axial force, and optionally, wherein the assembly further comprises a removable safety stopper disposed between the plunger proximal end and the proximal opening of the container to prevent the plunger from its movement inwardly with respect to the container until the stopper is removed.

2. A syringe assembly according to claim 1, wherein the receptacle constitutes the distal end of the plunger.

* * * * *